US00PP26240P2

(12) United States Plant Patent
de Groot

(10) Patent No.: US PP26,240 P2
(45) Date of Patent: Dec. 15, 2015

(54) ***HYPERICUM* PLANT NAMED 'RUIHYH004C'**

(50) Latin Name: *Hypericum×inodorum*
Varietal Denomination: Ruihyh004c

(71) Applicant: Henk C. A. de Groot, Amstelveen (NL)

(72) Inventor: Henk C. A. de Groot, Amstelveen (NL)

( * ) Notice: Subject to any disclaimer, the term of this patent is extended or adjusted under 35 U.S.C. 154(b) by 108 days.

(21) Appl. No.: 13/998,749

(22) Filed: Dec. 3, 2013

(51) Int. Cl.
*A01H 5/02* (2006.01)

(52) U.S. Cl.
USPC ..... Plt./442

(58) Field of Classification Search
USPC ..... Plt./442, 263.1, 226
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of *Hypericum×inodorum*, 'Ruihyh004c', that is characterized by its compact plant habit suitable for container growing, its medium sized berries that are creamy white in color and ovate in shape, and its medium sized light green sepals that are ovate in shape.

2 Drawing Sheets

Botanical classification: *Hypericum×inodorum.*
Variety denomination: 'Ruihyh004c'.

BACKGROUND OF THE INVENTION

The present invention relates to a new and distinct cultivar of *Hypericum×inodorum* and will be referred to hereafter by its cultivar name, 'Ruihyh004c'. 'Ruihyh004c' is a semi-evergreen shrub grown for use as a landscape plant and container plantings.

The new cultivar was derived from a controlled breeding program conducted by the Inventor in Hazerswoude, The Netherlands. The overall purpose of the breeding program was to develop new cultivars of *Hypericum* plants with unique berries and improved resistance to *Melampsora hypericorum.*

The new cultivar arose from a cross made by the Inventor in Hazerswoude, The Netherlands in April 2007 between an unnamed plant from the Inventor's breeding program, designated 'Ruihyd064A' as the female parent and 'Jolly Hypearl' (not patented) as the male parent. The Inventor selected 'Ruihyh004c' as a single unique plant amongst the seedlings that resulted from the above cross in autumn of 2008.

Asexual propagation of the new cultivar was first accomplished by the Inventor by vegetative stem cuttings in 2010 in Hazerswoude, The Netherlands. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Ruihyh004c' as a unique cultivar of *Hypericum.*

1. 'Ruihyh004c' exhibits a compact plant habit suitable for container growing.
2. 'Ruihyh004c' exhibits medium sized berries that are creamy white in color and ovate in shape.
3. 'Ruihyh004c' exhibits medium sized light green sepals that are ovate in shape.

The female parent of 'Ruihyh004c', 'Ruihyd064a', differs from 'Ruihyh004c' in having berries that are light pink in color and triangular in shape. The male parent of 'Ruihyh004c', 'Jolly Hypearl', is similar to 'Ruihyh004c' in having berries that are ovate in shape. 'Jolly Hypearl', differs from 'Ruihyh004c' in having berries that are red in color, narrower in width and longer in length. 'Ruihyh004c' can be most closely compared to the cultivar 'Ella Hypearl' (not patented). 'Ella Hypearl' differs from 'Ruihyh004c' in having berries that are slightly darker in color and smaller in size. 'Ruihyh004c' can also be compared to its sibling cultivar 'Ruihyh004b' (U.S. Plant patent application Ser. No. 13/998,748). 'Ruihyh004b' is similar to 'Ruihyh004c' in having a compact plant habit. 'Ruihyh004b' differs from 'Ruihyh004c' in having berries that are green in color, in having sepals that are smaller in size, and in having stamens that are held in a more upright position.

BRIEF DESCRIPTION OF THE DRAWINGS

The accompanying colored photographs illustrate the overall appearance and distinct characteristics of the new *Hypericum*. The plants in the photographs were taken of plants two years in age as grown in a one-gallon container in a greenhouse in Lelystad, The Netherlands.

The photograph in FIG. 1 provides a side view of 'Ruihyh004c' in bloom.

Figure 1:
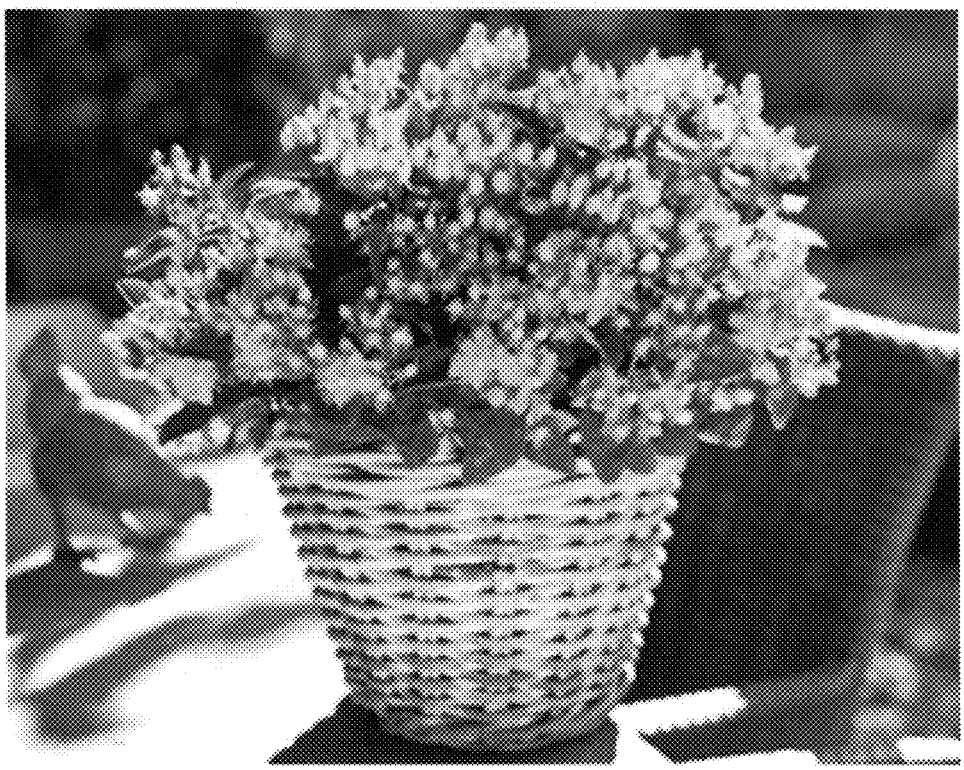
Figure 2:
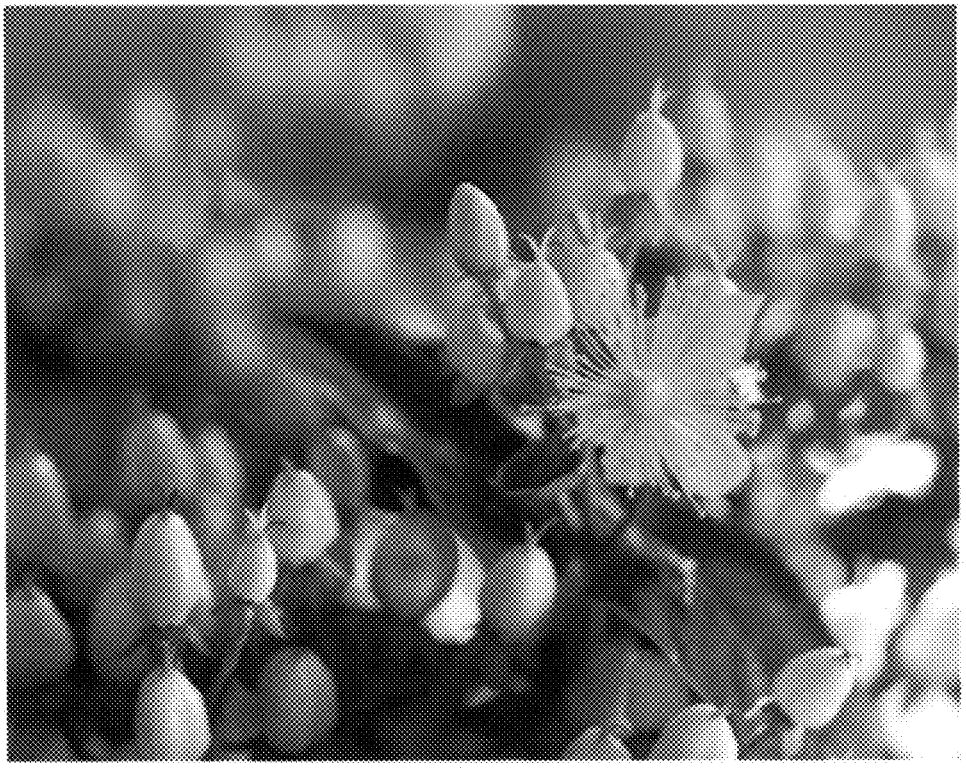

The photograph in FIG. 2 provides a close-up view of a flower and berries of 'Ruihyh004c'.

The colors in the photographs are as close as possible with the digital photography techniques available and the color values cited in the detailed botanical description accurately describe the colors of the new *Hypericum.*

DETAILED BOTANICAL DESCRIPTION

The following is a detailed description of two year-old plants of the new cultivar as grown outdoors in 2-gallon containers in Davidsonville, Md. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—From July to September in The Netherlands.

*Plant type.*—Semi-evergreen shrub.

*Plant habit.*—Compact with suitability for container growing.

*Height and spread.*—Reaches an average of 35 cm in height and an average of 50 cm in width.

*Cold hardiness.*—Observed to be hardy to at least −10° C.

*Diseases.*—Has shown tolerance to *Melampsora hypericorum.*

*Root description.*—Fibrous and fine.

*Propagation.*—Vegetative stem cuttings.

*Growth rate.*—Moderate, typical for cultivars of *Hypericum×inodorum.*

Stem description:

*Shape.*—Round.

*Stem color.*—New growth; 144B to 144C, maturing branches become a blend of 165A and 166A as they become woody.

*Stem size.*—Main stems; an average of 9 mm in diameter and 35 cm in length, lateral branches; an average of 20 cm in length and 3.5 mm in width.

*Stem surface.*—Glabrous when young and maturing, exfoliating when mature.

*Internode length.*—Average of 4.2 cm.

*Branching.*—Freely branched with lateral branches upright to about a 45° angle from vertical.

Foliage description:

*Leaf shape.*—Elliptic to ovate.

*Leaf division.*—Simple.

*Leaf base.*—Cuneate.

*Leaf apex.*—Acute.

*Leaf fragrance.*—None.

*Leaf venation.*—Pinnate, not conspicuous, 139A on upper surface and 138A to 138B on lower surface.

*Leaf margins.*—Entire.

*Leaf arrangement.*—Opposite, slightly cupped downward, aspect is primarily horizontal.

*Leaf attachment.*—Sessile.

*Leaf substance.*—Moderate.

*Leaf surface.*—Glabrous on upper and lower surface.

*Leaf size.*—Up to 7 cm in length and up to 4.1 cm in width.

*Leaf color.*—Newly expanded and mature leaves; upper surface 139A, lower surface 138A to 138B.

Inflorescence description:

*Inflorescence type.*—Terminal compound corymb.

*Flower buds.*—Conical in shape with acute to rounded apex, an average of 7 mm in length and 6 mm in width prior to opening, calyx portion is wrapped around petals and 144A in color, petal portion emerges a blend of 154A and 2A in color and changes to 12A prior to opening.

*Flower fragrance.*—None detected.

*Flower quantity.*—An average of 18 per lateral branch.

*Flower type.*—Complete and rotate with reflexed petals and prominent stamens and ovary.

*Flower aspect.*—Upward facing.

*Flower lastingness.*—An average of 5 days.

*Flower size.*—Average of 2 cm in diameter and 1 cm in depth.

*Petals.*—5, obovate to oval in shape, un-fused, curved inward and becoming horizontal, upper and lower surface glabrous and satiny, entire margin, truncate base, rounded apex with single slight notch, about 9 mm in length and 6 mm in width, upper and lower surface a blend of 12A and 13A in color.

*Calyx.*—Reflexed, un-fused sepals, about 1.9 cm in diameter and 4 mm in depth.

*Sepals.*—5, elliptic to oval in shape, upper surface; a blend of 144A to 144B and 143A, lower surface 144A in color, glabrous on upper and lower surface, an average of 1 cm in length and 6 mm in width, entire margin, truncate base, acute apex.

*Peduncles.*—An average of 1 mm in length, 2 mm in width, 144A in color, glabrous surface.

*Pedicels.*—An average of 8 mm in length, 2 mm in width, 144A in color, glabrous surface.

Reproductive organs:

*Gynoecium.*—Compound pistil about 7 mm in length and 4 mm in width, styles; 3C in color and about 2 mm in length and 0.2 mm in width, stigmas; 3, 17A in color about 1 mm in diameter, ovary is superior and 3C in color, about 5 mm in length and 4 mm in width.

*Androecium.*—Numerous stamens (about 100, arranged in 5 tufts), spreading outward from base of ovary extending about 1.4 cm in diameter, filaments are 9A in color, about 7 mm in length and 0.2 mm in width, anthers are 22A in color, dorsifixed, about 1 mm in length and width, pollen is low in quantity and 22A in color.

*Fruit.*—Ovate in shape with a mucronate apex, glabrous and satiny surface, an average of 1.3 cm in length and 9 mm in width, 11D in color when mature.

It is claimed:

1. A new and distinct cultivar of *Hypericum* plant named 'Ruihyh004c' as herein illustrated and described.

* * * * *